(12) United States Patent
Marques Borges et al.

(10) Patent No.: US 11,375,749 B2
(45) Date of Patent: Jul. 5, 2022

(54) ADAPTABLE AEROSOL-GENERATING SYSTEM

(71) Applicant: Philip Morris Products S.A., Neuchatel (CH)

(72) Inventors: Miguel Marques Borges, Yverdon-les-Bains (CH); Marie Farine, Sugiez (CH); Dani Ruscio, Cressier (CH); Ali Murat Saygili, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 394 days.

(21) Appl. No.: 16/616,809

(22) PCT Filed: Jun. 8, 2018

(86) PCT No.: PCT/EP2018/065226
§ 371 (c)(1),
(2) Date: Nov. 25, 2019

(87) PCT Pub. No.: WO2018/224677
PCT Pub. Date: Dec. 13, 2018

(65) Prior Publication Data
US 2020/0107572 A1 Apr. 9, 2020

(30) Foreign Application Priority Data
Jun. 9, 2017 (EP) ..................................... 17175350

(51) Int. Cl.
*A24B 15/167* (2020.01)
*A24F 40/30* (2020.01)
(Continued)

(52) U.S. Cl.
CPC ............ *A24F 40/30* (2020.01); *A24B 15/167* (2016.11); *A24F 40/42* (2020.01); *A24F 40/46* (2020.01);
(Continued)

(58) Field of Classification Search
CPC ........ A24F 40/46; A24F 40/465; A24F 40/30; A61M 15/06
See application file for complete search history.

(56) References Cited

U.S. PATENT DOCUMENTS 5,224,498 A 7/1993 Deevi et al.
9,532,603 B2 * 1/2017 Plojoux ................. A24F 40/485
(Continued)

FOREIGN PATENT DOCUMENTS

EP 2 921 065 A1 9/2015
RU 2 604 022 C2 12/2016
(Continued)

OTHER PUBLICATIONS

Combine Russian Federation Office Action and Search Report dated Oct. 1, 2021 in Russian Federation Patent Application No. 2019138517/03(076016) (with English translation), 12 pages.
(Continued)

*Primary Examiner* — Neil Abrams
(74) *Attorney, Agent, or Firm* — Oblon, McClelland, Maier & Neustadt, L.L.P.

(57) ABSTRACT

An aerosol-generating system is provided, including a cartridge and an aerosol-generating device; the cartridge including a cartridge body defining a substrate compartment and a heater cavity, and an aerosol-forming substrate positioned within the substrate compartment; the aerosol-generating device including a housing defining a device cavity configured to receive at least a portion of the cartridge body, and an elongate electric heater disposed in the device cavity;
(Continued)

and a thermally conductive sheath secured over the elongate electric heater such that the electric heater is substantially enclosed within the thermally conductive sheath along at least part of a length thereof; in which the thermally conductive sheath and the electric heater are configured to extend into the heater cavity of the cartridge when the cartridge is received in the device cavity such that the substrate compartment of the cartridge is heated by the electric heater via the thermally conductive sheath.

18 Claims, 4 Drawing Sheets

(51) Int. Cl.

| | | |
|---|---|---|
| *A61M 15/06* | (2006.01) | |
| *A24F 40/42* | (2020.01) | |
| *A24F 40/46* | (2020.01) | |
| *A61M 11/04* | (2006.01) | |
| *H05B 1/02* | (2006.01) | |
| *A24F 40/20* | (2020.01) | |

(52) U.S. Cl.
CPC .............. *A61M 15/06* (2013.01); *A24F 40/20* (2020.01); *A61M 11/042* (2014.02); *A61M 2205/3368* (2013.01); *A61M 2205/8206* (2013.01); *H05B 1/0244* (2013.01); *H05B 2203/021* (2013.01)

(56) References Cited

U.S. PATENT DOCUMENTS

| | | | |
|---|---|---|---|
| 10,206,430 B2 * | 2/2019 | Mironov | A61M 11/08 |
| 10,334,883 B2 * | 7/2019 | Silvestrini | A24F 40/30 |
| 10,645,973 B2 * | 5/2020 | Silvestrini | A24F 40/30 |
| 10,668,058 B2 * | 6/2020 | Rose | A24F 42/20 |
| 10,772,357 B2 * | 9/2020 | Saygili | A24B 15/167 |
| 10,888,123 B2 * | 1/2021 | Silvestrini | A24F 40/42 |
| 10,966,461 B2 * | 4/2021 | Plojoux | A24F 40/40 |
| 11,229,235 B2 * | 1/2022 | Saygili | A24F 40/57 |
| 2008/0149118 A1 | 6/2008 | Oglesby et al. | |
| 2015/0053217 A1 | 2/2015 | Steingraber et al. | |
| 2016/0324215 A1 | 11/2016 | Mironov et al. | |
| 2017/0042243 A1 | 2/2017 | Plojoux et al. | |
| 2017/0095002 A1 | 4/2017 | Silvestrini | |
| 2017/0119049 A1 | 5/2017 | Blandino et al. | |
| 2017/0143041 A1 | 5/2017 | Batista et al. | |
| 2018/0007971 A1 | 1/2018 | Plojoux et al. | |
| 2018/0235278 A1 | 8/2018 | Mahler et al. | |
| 2018/0255833 A1 | 9/2018 | Nicolas et al. | |
| 2020/0107572 A1 * | 4/2020 | Marques Borges | A24F 40/30 |
| 2020/0367569 A1 * | 11/2020 | Farine | A24F 40/46 |

FOREIGN PATENT DOCUMENTS

| | | |
|---|---|---|
| WO | WO 2008/121610 A1 | 10/2008 |
| WO | WO 2015/101479 A1 | 7/2015 |
| WO | WO 2015/197627 A1 | 12/2015 |
| WO | WO 2016/156509 A1 | 10/2016 |
| WO | WO 2017/042081 A1 | 3/2017 |
| WO | WO 2017/108983 A1 | 6/2017 |
| WO | WO 2017/108987 A1 | 6/2017 |
| WO | WO 2017/108991 A1 | 6/2017 |
| WO | WO 2017/108992 A1 | 6/2017 |

OTHER PUBLICATIONS

International Search Report and Written Opinion dated Dec. 14, 2018 in PCT/EP2018/065226 filed Jun. 8, 2018.

* cited by examiner

ADAPTABLE AEROSOL-GENERATING SYSTEM

The present invention relates to an aerosol-generating system comprising a cartridge containing an aerosol-forming substrate, and an aerosol-generating device. In particular, the invention relates to an aerosol-generating system comprising a cartridge having a cartridge body defining a substrate compartment and a heater cavity, and an aerosol-generating device having a device cavity for receiving at least a portion of the cartridge body; an elongate electric heater located in the device cavity and configured to extend into the heater cavity when the cartridge is received in the device cavity. The present invention also relates to an aerosol-generating device for use in such a system, and to a kit for such an aerosol-generating system. The present invention further relates to a method of adapting an aerosol-generating device for use with a cartridge to form such an aerosol-generating system.

Known handheld aerosol-generating systems typically comprise an aerosol-generating device comprising a battery, control electronics and an electric heater for heating an aerosol-generating article, such as a cartridge, designed specifically for use with the aerosol-generating device. In some examples, the aerosol-generating article comprises an aerosol-forming substrate, such as a tobacco rod or a tobacco plug, and the heater contained within the aerosol-generating device is inserted into or around the aerosol-forming substrate when the aerosol-generating article is inserted into the aerosol-generating device. In an alternative aerosol-generating system, the aerosol-generating article may comprise a capsule containing an aerosol-forming substrate, such as loose tobacco, or a liquid storage portion containing a liquid aerosol-forming substrate.

In another alternative aerosol-generating system, the aerosol-generating article may comprise a cartridge in which the aerosol-forming substrate comprises a nicotine source and an acid source. In use, the nicotine and the acid are reacted with one another in the gas phase to form an aerosol of nicotine salt particles that is inhaled by the user. Devices for delivering aerosol to a user comprising a nicotine source and a volatile delivery enhancing compound source are known. For example, WO 2008/121610 A1 discloses devices in which nicotine and an acid, such as pyruvic acid, are reacted with one another in the gas phase to form an aerosol of nicotine salt particles that is inhaled by the user.

Aerosol-generating systems comprising a cartridge having a cartridge body defining a substrate compartment and a heater cavity, and an aerosol-generating device having an elongate electric heater configured to extends into the heater cavity of the cartridge are known. Differences in the dimensions of the electric heater and the heater cavity may hinder the transfer of heat from the electric heater to the cartridge. These differences, or the structure of the electric heater, may also lead to the occurrence of hot spots on the cartridge which may in turn lead to inconsistent heating of the aerosol-forming substrate contained therein. Furthermore, existing electric heaters may be damaged during insertion into the heater cavity of the cartridge unless care is taken to ensure that the electric heater and the cartridge are properly aligned and excess force is not used.

It would be desirable to provide an aerosol-generating system comprising a cartridge and an aerosol-generating device with an electric heater configured to extend into a heater cavity in the cartridge that enables the cartridge to be heated more uniformly by the electric heater. It would also be desirable to provide an aerosol-generating system comprising a cartridge and an aerosol-generating device with an electric heater configured to extend into a heater cavity in the cartridge that reduces the risk of damage to the electric heater during insertion into the heater cavity.

According to a first aspect of the present invention, there is provided an aerosol-generating system comprising a cartridge and an aerosol-generating device. The cartridge comprises a cartridge body defining a substrate compartment and a heater cavity; and an aerosol-forming substrate positioned within the substrate compartment. The aerosol-generating device comprises a housing defining a device cavity for receiving at least a portion of the cartridge body; an elongate electric heater located in the device cavity; and a thermally conductive sheath secured over the elongate electric heater such that the electric heater is substantially enclosed within the thermally conductive sheath along at least part of its length. The thermally conductive sheath and the electric heater are configured to extend into the heater cavity of the cartridge when the cartridge is received in the device cavity such that, in use, the substrate compartment of the cartridge is heated by the electric heater via the thermally conductive sheath.

Advantageously, this may improve the efficiency of heat transfer from the electric heater to the cartridge. The sheath may also act to spread the heat from the electric heater over a wider surface area than with the electric heater alone, which may reduce the incidence of hot spots on the cartridge and allow for more even, or homogenised, heating of the aerosol-forming substrate. This may lead to more consistent aerosol delivery. Moreover, the sheath may act as a protective covering over the electric heater to reduce the risk of damage to the electric heater during insertion of a cartridge into the device cavity. This may be enhanced by forming the sheath from material which is stiffer, harder, or stiffer and harder than may be possible with the electric heater.

Further, by using a sheath, the heating performance of the device may be tailored for a given cartridge without the need for a redesign of the electric heater or the device itself. This is because the geometry of sheath used may be varied according to the configuration of the cartridge with which the device is intended for use, for example according to the dimensions of the heater cavity or the position of the substrate compartment within the cartridge. This may also improve the ease with which a cartridge may be inserted into the device cavity, since, by more closely following the dimensions of the heater cavity than the underlying electric heater, the sheath may act as a guide for proper placement of the cartridge in the device cavity. The sheath may also allow the size of the heater cavity in the cartridge to be increased for a given electric heater thickness. This may be of particular benefit when a thin electric heater is used, since it may be difficult to consistently manufacture cartridges having the correspondingly narrow heater cavities which would otherwise be required for effective heat transfer.

The system comprises a cartridge. The cartridge is consumable. The cartridge and the aerosol-generating device are configured to engage and cooperate with one another to form the aerosol-generating system for the in situ generation of an aerosol. The cartridge may be removably coupled to the aerosol-generating device. As used herein, the term 'removably coupled' is used to mean that the cartridge and device can be coupled and uncoupled from one another without significantly damaging either the device or cartridge. The cartridge may be removed from the aerosol-generating device when the aerosol-forming substrate has been consumed. The cartridge may be disposable. The cartridge may be reusable. The cartridge may be refillable with aerosol-forming substrate. The cartridge may be replaceable in the aerosol-generating device.

As used herein, the term 'aerosol-forming substrate' relates to a substrate capable of releasing volatile compounds that can form an aerosol. Such volatile compounds may be released by heating the aerosol-forming substrate.

As used herein, the term "aerosol-generating device" refers to a device that interacts with a cartridge comprising an aerosol-forming substrate to generate an aerosol.

As used herein, the term "substantially enclosed" means that the part of the length of the electric heater which is substantially enclosed within the sheath is covered by the sheath over at least 70 percent of the outer surface area of the electric heater, preferably at least 80 percent of its outer area, more preferably at least 90 percent of its outer area. This includes arrangements of sheath which extend around the entire circumference of the electric heater, as well as arrangements of sheath having one or more openings along its length or around its circumference, for example an open-sided sheath.

In certain embodiments, the thermally conductive sheath covers at least 30 percent of the outer surface area of the electric heater. For example, the thermally conductive sheath may substantially enclose the electric heater over about 30 percent of the length of the electric heater. In other examples, the thermally conductive sheath may extend over substantially the entire length of the electric heater and include one or more windows or openings which reduce the amount of the outer surface area of the electric heater which is covered by the sheath to about 30 percent. Where the thermally conductive sheath covers at least 30 percent of the outer surface area of the electric heater, it will be understood that the thermally conductive sheath may extend over anywhere from about 30 percent of the length of the electric heater to 100 percent of the length of the electric heater. Where the thermally conductive sheath comprises one or more windows or openings, the one or more windows or openings are preferably located in the distal portion of the thermally conductive sheath, for example towards the distal end of the thermally conductive sheath. In this manner, the one or more windows or openings may reduce the amount of thermally conductive material required while ensuring good thermal contact between the electric heater and the cartridge towards the proximal end of the thermally conductive sheath.

As used herein, the term "thermally conductive sheath" refers to a sheath having a thermal conductivity of at least 40 W/m·K, preferably or at least 100 W/m·K. Unless otherwise stated, thermal conductivity values referred to herein are thermal conductivity values as measured in accordance with ASTM C1114-00.

The sheath may be thermally coupled to the electric heater via one or more intermediate components. Preferably, the sheath is in direct contact with the electric heater along at least part of the length of the sheath. The sheath may be thermally coupled to the cartridge via one or more intermediate components. Preferably, the sheath is in direct contact with the cartridge along at least part of the length of the sheath. In particularly preferred embodiments, the sheath is in direct contact with both the cartridge and the electric heater along at least part of the length of the sheath.

The sheath substantially encloses the electric heater along its least part of the length of the electric heater. In preferred embodiments, the sheath substantially encloses the electric heater along the entire length of the part of the electric heater which is configured to extend into the heater cavity of the cartridge. Preferably, the electric heater is substantially enclosed within the thermally conductive sheath along substantially the entire length of the electric heater. As used herein, the term "along substantially the entire length of the electric heater" refers to at least 80 percent of the length of the electric heater, preferably at least 90 percent of the length of the electric heater, more preferably at least 95 percent of the length of the electric heater.

The thermally conductive sheath may be permanently secured over the electric heater. Advantageously, the thermally conductive sheath may be removably secured over the electric heater. With this arrangement, the sheath may be removed and replaced with a new sheath independently from the rest of the device, for example after a certain number of uses. This may allow the performance of the device to be maintained without the need for cleaning of the electric heater or the thermally conductive sheath. This may allow the sheath to be swapped with a sheath according to the requirements of a given cartridge. For example, the sheath may be replaced with a sheath having different dimensions or which is formed with a different material.

The sheath may be formed from a plurality of components. For example, the sheath may be formed from two or more discrete segments of sheath which are joined together. Preferably, the sheath is formed from a single thermally conductive component.

In preferred embodiments, the sheath is formed from a single sheet of thermally conductive material which has been bent or folded to shape. This allows for simple sheath construction and manufacture.

In particularly preferred embodiments, the sheath comprises a sheet of thermally conductive material which has been bent or folded along a single bend line such that the sheath comprises two opposed sheath walls, between which the electric heater is substantially enclosed along at least part of its length, and an opening opposite the single bend line. This has been found to provide a particularly simple, yet effective, structure. The opening may make it easier to place the sheath over the electric heater during manufacture or assembly.

Preferably, the sheet of thermally conductive material is elastic and bent or folded such that the bend line provides a spring force to bias the sheath walls apart at the opening. This may improve the ease with which the sheath is positioned over the electric heater, either by a user or during manufacture. For example, the sheet of thermally conductive material may be bent or folded into a substantially V-shape. With this arrangement, the sheath walls are biased apart at the opening. The opposed walls of the sheath may then be closed together over the electric heater. For example, where the electric heater is flat, the opposed walls of the sheath may then be closed together over the electric heater such that the sheath walls are parallel.

The sheath may have a substantially smooth outer surface. This may reduce the insertion force required to insert the sheath into the heater cavity of a cartridge and, therefore, the insertion force required to insert the cartridge into the device cavity.

In preferred embodiments, the sheath comprises a plurality of ridges on its outer surface.

In particularly preferred embodiments, the sheath comprises a corrugated sheet of thermally conductive material. With this arrangement, the corrugated structure allows the sheath to flex across its thickness to conform to the outer surface of the electric heater and to the inner surface of the heater cavity of the cartridge. This may improve the consistency of thermal contact between the electric heater and the cartridge by compensating for the manufacturing tolerances of the electric heater, the sheath, and the cartridge. This may allow more efficient heat transfer between the electric heater and the cartridge. It may also help to ensure more consistent performance between different cartridges or different devices. It may also enable reliable contact between the sheath and the cartridge while limiting the insertion force between the cartridge and the device. The corrugations may also increase the moment of inertia of the sheath relative to a flat sheet having the same sheet thickness. This increases the stiffness of the sheath and may reduce the risk of bending of the electric heater and the sheath during insertion of the cartridge into the device cavity. It may also decrease the amount of material required to manufacture a sheath of a given stiffness or thickness.

Preferably the corrugated sheet of thermally conductive material comprises a first set of corrugations extending along a first direction and a second set of corrugations extending along a second direction which is at an angle to the first direction. With this arrangement, the stiffness of the sheath may be maintained in all directions. This differs from an arrangement in which each corrugation extends in a single direction across the entire width or length of the sheath, in which the sheath may be more susceptible to bending under a bending moment is applied around an axis which is parallel to the corrugation direction. In some embodiments, the corrugations are arranged in a chevron pattern. The sheet may be corrugated such that the corrugations on the resulting sheet are symmetrical about one or more axes. For example, the corrugations may be symmetrical about the longitudinal axis of the sheath.

The thermally conductive sheath may be made from any suitable thermally conductive material or materials. Preferably, the thermally conductive sheath is formed from a metal or alloy. Suitable materials include, but are not limited to, aluminium, copper and steel, or any combination thereof.

The sheath may have any suitable thickness. In certain preferred embodiments, the sheath has a thickness of from about 0.20 mm to about 0.35 mm, preferably from about 0.22 mm to about 0.30 mm, more preferably from about 0.25 mm to about 0.29 mm, most preferably about 0.27 mm. These ranges have been found to provide a particularly desirable combination of effective heat transfer and protection of the electric heater without excessively increasing the weight of the device, or the insertion force required to insert a cartridge into the device cavity.

As used herein, the term "thickness" with respect to the sheath refers to the thickness of a wall of the sheath, rather than the total width or depth of the sheath as a whole. For example, where the sheath is made from a sheet of thermally conductive material, the term "thickness" refers to thickness of the sheet itself.

The sheath may be secured in the cavity of the device by any suitable connection. For example, where the sheath is removably secured over the electric heater by a clip or a retaining pin. In preferred embodiments, the sheath is provided with a sheath mount by which the sheath is secured over the electric heater. The sheath mount is preferably at the distal end of the sheath. Preferably, the sheath mount is configured to press-fit against a retainer at the distal end the device cavity. In such embodiments, the sheath mount may have any suitable shape. For example, the sheath mount may be generally disc shaped. The retainer may comprise a clip within which the sheath mount is retained. The retainer may comprise a raised lip against which the sheath mount is press fit.

Where the sheath comprises a sheet of thermally conductive material which has been bent or folded to shape such that the sheath comprises two or more sheath walls within which the electric heater is substantially enclosed, the sheath mount may be provided at the distal end of one or more of the sheath walls. Advantageously, the sheath mount comprises a first sheath mount portion at the distal end of a first sheath wall and a second sheath mount portion at the distal end of a second sheath wall. With this arrangement, the sheath mount is formed when the sheath walls are brought together around the electric heater and the sheath mount portions combine to define the sheath mount. This may help the sheath mount to hold the sheath walls together against the electric heater as well as retaining the sheath within the device cavity.

The sheath mount may be made from any suitable high temperature resistant material. Preferably, the sheath mount is made from a material having low thermal conductivity. For example, the sheath mount may comprise, or be made of, PEEK.

The aerosol-generating device according to the present invention comprises an elongate electric heater. The electric heater may be a single electric heater. This advantageously provides for a simple device construction.

The electric heater is configured as an internal heater that in use is positioned internally to the cartridge. The aerosol-generating device may advantageously comprise a guide portion configured for engagement with the cartridge to facilitate proper alignment of the electric heater with the heater cavity of the cartridge.

Advantageously, the electric heater is configured to heat the cartridge to a temperature of below about 250 degrees Celsius. Preferably, the electric heater is configured to heat the cartridge to a temperature of between about 80 degrees Celsius and about 150 degrees Celsius. Advantageously, the elongate electric heater is in the form of a heater blade having a width that is greater than the thickness thereof. In such embodiments, the heater cavity in the cartridge may be configured as an elongate slot.

The electric heater may be a resistive heater. Alternatively, the electric heater may be an inductive heater. Preferably, the electric heater comprises an electric heating element comprising an electrically resistive material. The electric heating element may comprise a non-elastic material, for example a ceramic sintered material, such as alumina ($Al_2O_3$) and silicon nitride ($Si_3N_4$), or printed circuit board or silicon rubber. Alternatively, the electric heating element may comprise an elastic, metallic material, for example an iron alloy or a nickel-chromium alloy.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physico-chemical properties required.

The electric heating element may be formed using a metal having a defined relationship between temperature and resistivity. In such embodiments, the metal may be formed as a track between two layers of suitable insulating materials. An electric heating element formed in this manner may be used both as a heater and a temperature sensor.

Preferably, the electric heater does not project from the aerosol-generating device.

The aerosol-generating system may further comprise a power supply for supplying power to the electric heater and a controller configured to control a supply of power from the power supply to the electric heater. Any suitable electronic circuitry may be used as the controller. The controller may be programmable.

The power supply may be a DC voltage source. In preferred embodiments, the power supply is a battery. For example, the power supply may be a Nickel-metal hydride battery, a Nickel cadmium battery, or a Lithium based battery, for example a Lithium-Cobalt, a Lithium-Iron-Phosphate or a Lithium-Polymer battery. The power supply may alternatively be another form of charge storage device such as a capacitor. The power supply may require recharging and may have a capacity that allows for the storage of enough energy for use of the aerosol-generating device with one or more aerosol-generating articles.

The aerosol-generating device may comprise one or more temperature sensors configured to sense the temperature of the electric heater and the temperature of the substrate compartment of the cartridge. In such embodiments, the controller may be configured to control a supply of power to the heater based on the sensed temperature The cartridge may be received entirely within the device cavity of the aerosol-generating device or partially within the device cavity of the aerosol-generating device. For example, the length of the device cavity of the aerosol-generating device is less than the length of the cartridge so that when the cartridge is received in the cavity of the aerosol-generating device the proximal or downstream end of the cartridge projects from the cavity of the aerosol-generating device.

Preferably, the device cavity of the aerosol-generating device is substantially cylindrical.

As used herein with reference to the present invention, the terms "cylinder" and "cylindrical" refer to a substantially right circular cylinder with a pair of opposed substantially planar end faces.

Preferably, the device cavity of the aerosol-generating device has a diameter substantially equal to or slightly greater than the diameter of the cartridge.

The cartridge comprises a substrate compartment in which an aerosol-forming substrate is positioned. The substrate compartment may contain a single aerosol-forming substrate. The substrate compartment may contain a plurality of aerosol-forming substrates. Where the substrate compartment contains a plurality of aerosol-forming substrates, these may be stored separately or together. In preferred embodiments, the cartridge comprises a nicotine source and an acid source for use in an aerosol-generating system for the in situ generation of an aerosol comprising nicotine salt particles. As used herein with reference to the present invention, by "in situ" it is meant that, in use, nicotine vapour released from the nicotine source and lactic acid vapour released from the lactic acid source react with one another in the gas phase within the aerosol-generating system according to the present invention to form an aerosol comprising nicotine lactate salt particles.

As used herein with reference to the invention, the term "nicotine", is used to describe nicotine, nicotine base or a nicotine salt. In embodiments in which a carrier material is impregnated with nicotine base or a nicotine salt, the amounts of nicotine recited herein are the amount of nicotine base or amount of ionised nicotine, respectively.

The nicotine source may comprise one or more of nicotine, nicotine base, a nicotine salt, such as nicotine-HCl, nicotine-bitartrate, or nicotine-ditartrate, or a nicotine derivative. The nicotine source may comprise natural nicotine or synthetic nicotine. The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof. For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof In certain embodiments, the nicotine source may comprise an aqueous solution of nicotine, nicotine base, a nicotine salt or a nicotine derivative and an electrolyte forming compound. Alternatively or in addition, the nicotine source may further comprise other components including, but not limited to, natural flavours, artificial flavours and antioxidants.

The nicotine source may comprise a first carrier material impregnated with nicotine. For example, the first carrier material may be impregnated with between about 1 milligram and about 50 milligrams of nicotine, preferably between about 1 milligram and about 40 milligrams of nicotine, more preferably, between about 3 milligrams and about 30 milligrams of nicotine, more preferably between about 6 milligrams and about 20 milligrams of nicotine, most preferably between about 8 milligrams and about 18 milligrams of nicotine.

The first carrier material may be impregnated with liquid nicotine or a solution of nicotine in an aqueous or non-aqueous solvent. The first carrier material may be impregnated with natural nicotine or synthetic nicotine.

Advantageously, the first carrier material has a density of between about 0.1 grams/cubic centimetre and about 0.3 grams/cubic centimetre. Advantageously, the first carrier material has a porosity of between about 15 percent and about 55 percent.

The first carrier material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The first carrier material acts as a reservoir for the nicotine.

Advantageously, the first carrier material is chemically inert with respect to nicotine.

The first carrier material may have any suitable shape and size. For example, the first carrier material may be in the form of a sheet or plug. The shape, size, density and porosity of the first carrier material may be chosen to allow the first carrier material to be impregnated with a desired amount of nicotine.

Advantageously, the first carrier material may further comprise a flavourant. Suitable flavourants include, but are not limited to, menthol. Advantageously, the first carrier material may be impregnated with between about 3 milligrams and about 12 milligrams of flavourant.

The acid source may comprise an organic acid or an inorganic acid.

Preferably, the acid source comprises an organic acid, more preferably a carboxylic acid, most preferably an alpha-keto or 2-oxo acid or lactic acid.

Advantageously, the acid source comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid, lactic acid and combinations thereof. Advantageously, the acid source comprises pyruvic acid or lactic acid. More advantageously, the acid source comprises lactic acid.

The acid source may comprise a second carrier material impregnated with acid.

Preferably, the acid source is a lactic acid source comprising a second carrier material impregnated with lactic acid. For example, the second carrier material may be impregnated with between about 2 milligrams and about 60 milligrams of lactic acid, between about 5 milligrams and about 50 milligrams of lactic acid, more preferably between about 8 milligrams and about 40 milligrams of lactic acid, most preferably between about 10 milligrams and about 30 milligrams of lactic acid.

Advantageously, the second carrier material has a density of between about 0.1 grams/cubic centimetre and about 0.3 grams/cubic centimetre. Advantageously, the second carrier material has a porosity of between about 15 percent and about 55 percent.

The second carrier material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The second carrier material acts as a reservoir for the acid.

Advantageously, the second carrier material is chemically inert with respect to the acid. The second carrier material may have any suitable shape and size. For example, the second carrier material may be in the form of a sheet or plug. The shape, size, density and porosity of the second carrier material may be chosen to allow the second carrier material to be impregnated with a desired amount of acid.

The first carrier material and the second carrier material may be the same or different.

Preferably the substrate compartment comprises a first compartment containing a nicotine source and a second compartment containing an acid source. The nicotine source preferably comprises a first carrier material impregnated with nicotine, as discussed above. Advantageously, the shape and of the first carrier material is similar to the shape and size of the first compartment of the cartridge. The acid source preferably comprises a second carrier material impregnated with acid, such as lactic acid. Advantageously, the shape and size of the second carrier material is similar to the shape and size of the second compartment of the cartridge.

Advantageously, the electric heater is configured to heat the first compartment and the second compartment of the cartridge to substantially the same temperature.

As used herein with reference to the invention, by "substantially the same temperature" it is meant that the difference in temperature between the first compartment and the second compartment of the cartridge measured at corresponding locations relative to the heater is less than about 3° C.

In use, heating the first compartment and the second compartment of the cartridge to a temperature above ambient temperature advantageously enables the vapour concentrations of the nicotine in the first compartment of the cartridge and the vapour pressure of acid in the second compartment of the cartridge to be controlled and balanced proportionally to yield an efficient reaction stoichiometry between the nicotine and the acid. Advantageously, this may improve the efficiency of the formation of nicotine salt particles and the consistency of delivery to a user. Advantageously, it may also reduce the delivery of unreacted nicotine and unreacted acid to a user.

The cartridge comprises a heater cavity for receiving the electric heater and the thermally conductive sleeve of the aerosol-generating device. Where the cartridge comprises two or more aerosol-forming substrates, such as a nicotine source and an acid source, stored in a first compartment and a second compartment, preferably the electric heater is configured to heat both the first compartment and the second compartment. In such embodiments, the heater cavity is advantageously located between the first compartment and the second compartment. That is the first compartment and the second compartment are disposed on either side of the heater cavity.

In preferred embodiments, the aerosol-forming substrate comprises a nicotine source and an acid source and the substrate compartment comprises a first compartment containing the nicotine source and a second compartment containing the acid source, wherein the first and second compartments are positioned on either side of the heater cavity.

Advantageously, the heater cavity extends from the distal end of the cartridge at least part way along the length of the cartridge. Advantageously, the heater cavity extends along the longitudinal axis of the cartridge.

The heater cavity may extend from the distal end of the cartridge to the proximal end of the cartridge. In such embodiments, the heater cavity has an open distal end and an open proximal end. The heater cavity may extend from the distal end of the cartridge part way along the length of the cartridge. In such embodiments, the heater cavity has an open distal end and a closed proximal end.

The heater cavity may be enclosed along its length.

The heater cavity may be at least partially open along its length. This may advantageously facilitate insertion of a heater into the heater cavity.

As further described and illustrated below, the cartridge preferably comprises a first compartment comprising a nicotine source and a second compartment comprising an acid source. As used herein, the term "first compartment" is used to describe one or more chambers or containers within the cartridge comprising the nicotine source. As used herein, the term "second compartment" is used to describe one or more chambers or containers within the cartridge comprising the acid source.

The first compartment may consist of one or more first chambers within the cartridge. The number and dimensions of the first chambers may be chosen to allow a desired amount of nicotine to be included in the cartridge. The second compartment may consist of one or more second chambers within the cartridge. The number and dimensions of the second chambers may be chosen to allow a desired amount of acid to be included in the cartridge.

The first compartment and the second compartment may abut one another. Alternatively, the first compartment and the second compartment may be spaced apart from one another.

In use, nicotine vapour is released from the nicotine source in the first compartment and acid is released from the acid source in the second compartment. The nicotine vapour reacts with the acid vapour in the gas phase to form an aerosol, which is delivered to a user. Preferably, the aerosol-generating system according to the present invention further comprises a reaction chamber downstream of the first compartment and the second compartment configured to facilitate reaction between the nicotine vapour and the acid vapour. The cartridge may comprise the reaction chamber. Alternatively, where the aerosol-generating system comprises a mouthpiece portion, the mouthpiece portion may comprise the reaction chamber.

As described further below, the first compartment and the second compartment may be arranged in series or parallel within the cartridge. Preferably, the first compartment and the second compartment are arranged in parallel.

As used herein, by "series" it is meant that the first compartment and the second compartment are arranged within the cartridge so that in use an air stream drawn through the cartridge passes through one of the first compartment and the second compartment and then passes through the other of the first compartment and the second compartment. Nicotine vapour is released from the nicotine source in the first compartment into the air stream drawn through the cartridge and acid is released from the acid source in the second compartment into the air stream drawn through the cartridge. The nicotine vapour reacts with the acid vapour in the gas phase to form an aerosol, which is delivered to a user.

In certain embodiments the cartridge may comprise an air inlet, a first compartment comprising the nicotine source in communication with the air inlet, a second compartment comprising the acid source in communication with the first compartment; and an air outlet, wherein the air inlet and the air outlet are in communication with each other and configured so that air may pass into the cartridge through the air inlet, through the cartridge and out of the cartridge through the air outlet.

As used herein with reference to the invention, the term "air inlet" is used to describe one or more apertures through which air may be drawn into a component or portion of a component of the aerosol-generating system. As used herein with reference to the invention, the term "air outlet" is used to describe one or more apertures through which air may be drawn out of a component or portion of a component of the aerosol-generating system.

In such embodiments, the first compartment and the second compartment are arranged in series from air inlet to air outlet within the cartridge. That is, the first compartment is downstream of the air inlet, the second compartment is downstream of the first compartment and the air outlet is downstream of the second compartment. In use, a stream of air is drawn into the housing through the air inlet, downstream through the first compartment and then the second compartment and out of the cartridge through the air outlet.

In such embodiments the cartridge may further comprise a third compartment in communication with: the second compartment; and the air outlet. In use in such embodiments, a stream of air is drawn into the cartridge through the air inlet, downstream through the first compartment, the second compartment and then the third compartment and out of the cartridge through the air outlet.

In such embodiments the cartridge may further comprise a mouthpiece in communication with: the second compartment or the third compartment, where present; and the air outlet. In use in such embodiments, a stream of air is drawn into the cartridge through the air inlet, downstream through the first compartment, the second compartment, the third compartment, where present, and then the mouthpiece and out of the cartridge through the air outlet.

In other embodiments the cartridge may comprise: an air inlet; a second compartment comprising the acid source in communication with the air inlet; a first compartment comprising the nicotine source in communication with the second compartment; and an air outlet, wherein the air inlet and the air outlet are in communication with each other and configured so that air may pass into the cartridge through the air inlet, through the cartridge and out of the cartridge through the air outlet.

In such embodiments the second compartment and the first compartment are arranged in series from air inlet to air outlet within the cartridge. That is, the second compartment is downstream of the air inlet, the first compartment is downstream of the second compartment and the air outlet is downstream of the first compartment. In use, a stream of air is drawn into the cartridge through the air inlet, downstream through the second compartment and then the first compartment and out of the cartridge through the air outlet.

In such embodiments the cartridge may further comprise a third compartment in communication with: the first compartment; and the air outlet. In use in such embodiments, a stream of air is drawn into the cartridge through the air inlet, downstream through the second compartment, the first compartment and then the third compartment and out of the cartridge through the air outlet.

In such embodiments the cartridge may further comprise a mouthpiece in communication with: the first compartment or the third compartment, where present; and the air outlet. In use in such embodiments, a stream of air is drawn into the cartridge through the air inlet, downstream through the second compartment, the first compartment, the third compartment, where present, and then the mouthpiece and out of the cartridge through the air outlet.

Where the first compartment and the second compartment are arranged in series within the cartridge, the second compartment is preferably downstream of the first compartment so that in use an air stream drawn through the cartridge passes through the first compartment and then passes through the second compartment.

Location of the second compartment comprising the acid source downstream of the first compartment comprising the nicotine source advantageously improves the consistency of the nicotine delivery of the aerosol-generating system. Without being bound by theory, it is believed that location of the lactic acid source downstream of the nicotine source reduces or prevents deposition of acid vapour released from the acid source on the nicotine source during use. This reduces fading over time of the nicotine delivery of the aerosol-generating system. It may also reduce the risk of undesired delivery of unreacted acid vapour to a user.

As used herein, by "parallel" it is meant that the first compartment and the second compartment are arranged within the cartridge so that in use a first air stream drawn through the cartridge passes through the first compartment and a second air stream drawn through the cartridge passes through the second compartment. Nicotine vapour is released from the nicotine source in the first compartment into the first air stream drawn through the cartridge and acid vapour is released from the acid source in the second compartment into the second air stream drawn through the cartridge. The nicotine vapour in the first air stream reacts with the acid vapour in the second air stream in the gas phase to form an aerosol, which is delivered to a user.

In certain embodiments the cartridge comprises: an air inlet; a first compartment comprising the nicotine source in communication with the air inlet; a second compartment comprising the acid source in communication with the air inlet; and an air outlet, wherein the air inlet and the air outlet are in communication with each other and configured so that air may pass into the cartridge through the air inlet, through the cartridge and out of the cartridge through the air outlet.

In such embodiments the first compartment and the second compartment are arranged in parallel from air inlet to air outlet within the cartridge. The first compartment and the second compartment are both downstream of the air inlet and upstream of the air outlet. In use, a stream of air is drawn into the cartridge through the air inlet, a first portion of the stream of air is drawn downstream through the first compartment and a second portion of the stream of air is drawn downstream through the second compartment.

In such embodiments the cartridge may further comprise a third compartment in communication with: one or both of the first compartment and the second compartment; and the air outlet. In such embodiments the cartridge may further comprise a mouthpiece in communication with: the first compartment and the second compartment, or the third compartment, where present; and the air outlet.

In other embodiments the cartridge comprises: a first air inlet; a second air inlet; a first compartment comprising the nicotine source in communication with the first air inlet; a second compartment comprising the acid source in communication with the second air inlet; and an air outlet, wherein the first air inlet, the second air inlet and the air outlet are in communication with each other and configured so that air may pass into the cartridge through the first air inlet, through the cartridge and out of the cartridge through the air outlet and air may pass into the cartridge through the first air inlet, through the cartridge and out of the cartridge through the air outlet.

In such embodiments the first compartment and the second compartment are arranged in parallel within the cartridge. The first compartment is downstream of the first air inlet and upstream of the air outlet and the second compartment is downstream of the second air inlet and upstream of the air outlet. In use, a first stream of air is drawn into the cartridge through the first air inlet and downstream through the first compartment and a second stream of air is drawn into the cartridge through the second air inlet and downstream through the second compartment.

The first air outlet of the first compartment of the cartridge is located at the proximal end of the first compartment of the cartridge. The first air inlet of the first compartment of the cartridge is located upstream of the first air outlet of the first compartment of the cartridge. The second air outlet of the second compartment of the cartridge is located at the proximal end of the second compartment of the cartridge. The second air inlet of the second compartment of the cartridge is located upstream of the second air outlet of the second compartment of the cartridge.

In such embodiments the cartridge may further comprise a third compartment in communication with: one or both of the first compartment and the second compartment; and the air outlet. In such embodiments the cartridge may further comprise a mouthpiece in communication with: the first compartment and the second compartment, or the third compartment, where present; and the air outlet.

Where the cartridge comprises a third compartment, the third compartment may comprise one or more aerosol-modifying agents. For example, the third compartment may comprise one or more sorbents, such as activated carbon, one or more flavourants, such as menthol, or a combination thereof.

Preferably the first compartment is an elongate first compartment having a length $L_1$ and a maximum transverse cross-sectional area $A_1$, the first compartment having a first air inlet and a first air outlet and containing a nicotine source comprising a first carrier material loaded with nicotine, as described above.

Preferably the second compartment is an elongate second compartment having a length $L_2$ and a maximum transverse cross-sectional area $A_2$, the second compartment having a second air inlet and a second air outlet and containing an acid source, wherein the first compartment and the second compartment are arranged in parallel within the cartridge and wherein the ratio $(L_1)^2:A_1$ is at least about 12:1 and wherein the ratio $(L_2)^2:A_2$ is at least about 12:1.

Advantageously, providing an elongate first compartment having a length $L_1$ and a maximum transverse cross-sectional area $A_1$ and an elongate second compartment having a length $L_2$ and a maximum transverse cross-sectional area $A_2$, wherein the ratio of $(L_1)^2$ to $A_1$ and $(L_2)^2$ to $A_2$ is at least about 12:1, facilitates uniform heating of the nicotine source in the first compartment and the acid source in the second compartment throughout use of the cartridge. This may also facilitate vaporisation of nicotine from the nicotine source in the first compartment and the vaporisation of acid from the acid source in the second compartment.

Preferably, the ratio of $(L_1)^2$ to $A_1$ is between about 12:1 and about 400:1.

Preferably, the ratio of $(L_1)^2$ to $A_1$ is at least about 15:1.

Preferably, the ratio of $(L_1)^2$ to $A_1$ is between about 15:1 and about 200:1.

Preferably, the ratio of $(L_1)^2$ to $A_1$ is at least about 20:1.

Preferably, the ratio of $(L_1)^2$ to $A_1$ is between about 20:1 and about 100:1.

For example, the ratio of $(L_1)^2$ to $A_1$ may be between about 25:1 and about 70:1 or between about 30:1 and about 70:1.

Preferably, the ratio of $(L_2)^2$ to $A_2$ is between about 12:1 and about 400:1.

Preferably, the ratio of $(L_2)^2$ to $A_2$ is at least about 15:1.

Preferably, the ratio of $(L_2)^2$ to $A_2$ is between about 15:1 and about 200:1.

Preferably, the ratio of $(L_2)^2$ to $A_2$ is at least about 20:1.

Preferably, the ratio of $(L_2)^2$ to $A_2$ is between about 20:1 and about 100:1.

For example, the ratio of $(L_2)^2$ to $A_2$ may be between about 25:1 and about 70:1 or between about 30:1 and about 70:1.

By providing the nicotine source and the acid source in separate compartments with separate air inlets and separate air outlets, may advantageously facilitate control of the reaction stoichiometry between the nicotine and the acid.

The ratio of nicotine and acid required to achieve an appropriate reaction stoichiometry may be controlled and balanced through variation of the volume of the first compartment relative to the volume of the second compartment.

The shape and dimensions of the first compartment of the cartridge may be chosen to allow a desired amount of nicotine to be housed in the cartridge.

The shape and dimensions of the second compartment of the cartridge may be chosen to allow a desired amount of acid to be housed in the cartridge.

The first compartment may have a length $L_1$, a width $W_1$ and a height $H_1$ and the second compartment may have a length $L_2$, a width $W_2$ and a height $H_2$. Advantageously, the ratio of $L_1$ to $W_1$ and $L_2$ to $W_2$ may be between about 2:1 and about 4:1, for example between about 5:2 and about 3:1. Advantageously, the ratio of $L_1$ to $H_1$ and $L_2$ to $H_2$ may be at least about 6:1.

Advantageously, the ratio of $L_1$ to $H_1$ and $L_2$ to $H_2$ may be between about 6:1 and about 30:1. Advantageously, the ratio of $L_1$ to $H_1$ and $L_2$ to $H_2$ may be between about 8:1 and about 16:1.

Advantageously, the first compartment of the cartridge has a length $L_1$ of between about 8 millimetres and about 40 millimetres, for example of between about 10 millimetres and about 20 millimetres. Advantageously, the first compartment of the cartridge has a width $W_1$ of between about 4 millimetres and about 6 millimetres. Advantageously, the first compartment of the cartridge has a height $H_1$ of between about 0.5 millimetres and about 2.5 millimetres.

The first compartment of the cartridge may have any suitable transverse cross-sectional shape. For example, the transverse cross-sectional shape of the first compartment may be circular, semi-circular, elliptical, triangular, square, rectangular or trapezoidal.

Advantageously, the second compartment of the cartridge has a length $L_2$ of between about 8 millimetres and about 40 millimetres, for example of between about 10 millimetres and about 20 millimetres. Advantageously, the second compartment of the cartridge has a width $W_2$ of between about 4 millimetres and about 6 millimetres. Advantageously, the second compartment of the cartridge has a height $H_2$ of between about 0.5 millimetres and about 2.5 millimetres.

The second compartment of the cartridge may have any suitable transverse cross-sectional shape. For example, the transverse cross-sectional shape of the second compartment may be circular, semi-circular, elliptical, triangular, square, rectangular or trapezoidal.

The shape and dimensions of the first compartment and the second compartment of the cartridge may be the same or different.

Advantageously, the ratio of the length of the first compartment $L_1$ to the length of the second compartment $L_2$ is between about 2:1 and about 1:2, more advantageously between about 1.2:1 and about 1:1.2.

Advantageously, the ratio of the maximum transverse cross-sectional area of the first compartment $A_1$ to the maximum transverse cross-sectional area of the first compartment $A_2$ is between about 2:1 and about 1:2, more advantageously between about 1.2:1 and about 1:1.2.

Advantageously, the shape and dimensions of the first compartment and the second compartment are substantially the same. Providing a first compartment and a second compartment having of substantially the same shape and dimensions may advantageously simplify manufacturing of the cartridge.

The first air inlet of the first compartment of the cartridge and the second air inlet of the second compartment of the cartridge may each comprise one or more apertures. For example, the first air inlet of the first compartment of the cartridge and the second air inlet of the second compartment of the cartridge may each comprise one, two, three, four, five, six or seven apertures.

The first air inlet of the first compartment of the cartridge and the second air inlet of the second compartment of the cartridge may comprise the same or different numbers of apertures.

Advantageously, the first air inlet of the first compartment of the cartridge and the second air inlet of the second compartment of the cartridge each comprise a plurality of apertures. For example, the first air inlet of the first compartment of the cartridge and the second air inlet of the second compartment of the cartridge may each comprise two, three, four, five, six or seven apertures.

Providing a first compartment having a first air inlet comprising a plurality of apertures and a second compartment having a second air inlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

The ratio of nicotine and acid required to achieve an appropriate reaction stoichiometry may be controlled and balanced through variation of the volumetric airflow through the first compartment of the cartridge relative to the volumetric airflow through the second compartment of the cartridge. The ratio of the volumetric airflow through the first compartment relative to the volumetric airflow through the second compartment may be controlled through variation of one or more of the number, dimensions and location of the apertures forming the first air inlet of the first compartment of the cartridge relative to the number, dimensions and location of the apertures forming the second air inlet of the second compartment of the cartridge.

In embodiments in which the acid source comprises lactic acid, advantageously the flow area of the second air inlet of the second compartment of the cartridge is greater than the flow area of the first air inlet of the first compartment of the cartridge.

As used herein with reference to the invention, the term "flow area" is used to describe the cross-sectional area of an air inlet or air outlet through which airflows during use. In embodiments in which an air inlet or air outlet comprises a plurality of apertures, the flow area of the air inlet or air outlet is the total flow area of the air inlet or air outlet and is equal to the sum of the flow areas of each of the plurality of apertures forming the air inlet or air outlet. In embodiments in which the cross-sectional area of an air inlet or air outlet varies in the direction of airflow, the flow area of the air inlet or air outlet is the minimum cross-sectional area in the direction of airflow.

Increasing the flow area of the second air inlet of the second compartment of the cartridge relative to the flow area of the first air inlet of the first compartment of the cartridge advantageously increases the volumetric airflow through the second air inlet compared to the volumetric airflow through the first air inlet.

In embodiments in which the acid source comprises lactic acid, preferably the ratio of the flow area of the first air inlet of the first compartment of the cartridge to the flow area of the second air inlet of the second compartment of the cartridge is between about 3:4 and about 1:2. More preferably, the ratio of the flow area of the first air inlet of the first compartment of the cartridge to the flow area of the second air inlet of the second compartment of the cartridge is between about 2:3 and about 1:2.

The flow area of the second air inlet of the second compartment of the cartridge may be increased relative to the flow area of the first air inlet of the first compartment of the cartridge by one or both of increasing the size of the one or more apertures forming the second air inlet relative to the size of the one or more apertures forming the first air inlet and increasing the number of apertures forming the second air inlet relative to the number of apertures forming the first air inlet.

Advantageously, the flow area of the second air inlet of the second compartment of the cartridge is increased relative to the flow area of the first air inlet of the first compartment of the cartridge by increasing the number of apertures forming the second air inlet relative to the number of apertures forming the first air inlet.

Advantageously, the first air inlet of the first compartment of the cartridge comprises between 2 and 5 apertures. Advantageously, the second air inlet of the second compartment of the cartridge comprises between 3 and 7 apertures.

Advantageously, the flow area of the first air inlet of the first compartment of the cartridge is between about 0.1 square millimetres and about 1.6 square millimetres, more advantageously between about 0.2 square millimetres and about 0.8 square millimetres.

In embodiments in which the first air inlet of the first compartment of the cartridge comprises a plurality of apertures, the apertures may have different flow areas so that the flow area of the first air inlet of the first compartment of the cartridge is divided unequally between the apertures forming the first air inlet.

In embodiments in which the first air inlet of the first compartment of the cartridge comprises a plurality of apertures, each of the apertures may have the same flow area so that the flow area of the first air inlet of the first compartment of the cartridge is divided equally between the apertures forming the first air inlet. Providing a first compartment having a first air inlet comprising a plurality of apertures having substantially the same flow area may advantageously simplify manufacturing of the cartridge.

The first air inlet of the first compartment of the cartridge may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

In embodiments in which the acid source comprises lactic acid, advantageously the flow area of the second air inlet of the second compartment of the cartridge is between about 0.2 square millimetres and about 2.4 square millimetres, more advantageously between about 0.4 square millimetres and about 1.2 square millimetres.

In embodiments in which the second air inlet of the second compartment of the cartridge comprises a plurality of apertures, the apertures may have different flow areas so that the total flow area of the second air inlet of the second compartment of the cartridge is divided unequally between the apertures forming the second air inlet.

In embodiments in which the second air inlet of the second compartment of the cartridge comprises a plurality of apertures, each of the apertures may have the same flow area so that the total flow area of the second air inlet of the second compartment of the cartridge is divided equally between the apertures forming the second air inlet. Providing a second compartment having a second air inlet comprising a plurality of apertures having substantially the same flow area may advantageously simplify manufacturing of the cartridge.

The second air inlet of the second compartment of the cartridge may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

Advantageously, the first compartment has a longitudinal first air inlet and the second compartment has a longitudinal second air inlet.

As used herein with reference to the invention, the term "longitudinal air inlet" is used to describe one or more apertures through which air may be drawn in a longitudinal direction into a component or portion of a component of the cartridge.

Advantageously, prior to first use of the cartridge, one or both of the first air inlet of the first compartment and the second air inlet of the second compartment may be sealed by one or more removable or frangible barriers. For example, one or both of the first air inlet of the first compartment and the second air inlet of the second compartment may be sealed by one or more peel-off or pierceable seals.

The one or more removable or frangible barriers may be formed from any suitable material. For example, the one or more removable or frangible barriers may be formed from a metal foil or film.

The first air outlet of the first compartment of the cartridge and the second air outlet of the second compartment of the cartridge may each comprise one or more apertures. For example, the first air outlet of the first compartment of the cartridge and the second air outlet of the second compartment of the cartridge may each comprise one, two, three, four, five, six or seven apertures.

The first air outlet of the first compartment of the cartridge and the second air outlet of the second compartment of the cartridge may comprise the same or different numbers of apertures.

Advantageously, the first air outlet of the first compartment of the cartridge and the second air outlet of the second compartment of the cartridge may each comprise a plurality of apertures. For example, the first air outlet of the first compartment of the cartridge and the second air outlet of the second compartment of the cartridge may each comprise two, three, four, five, six or seven apertures. Providing a first compartment having a first air outlet comprising a plurality of apertures and a second compartment having a second air outlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

In embodiments in which the first air outlet of the first compartment of the cartridge comprises a plurality of apertures, advantageously the first air outlet comprises between 2 and 5 apertures. In embodiments in which the second air outlet of the second compartment of the cartridge comprises a plurality of apertures, advantageously, the second air outlet comprises between 3 and 7 apertures.

Advantageously, the first air outlet of the first compartment of the cartridge of the cartridge assembly and the second air outlet of the second compartment of the cartridge of the cartridge assembly may each comprise a single aperture. Providing a first compartment having a first air outlet comprising a single aperture and a second compartment having a second air outlet comprising a single aperture may advantageously simplify manufacturing of the cartridge.

The ratio of nicotine and acid required to achieve an appropriate reaction stoichiometry may be controlled and balanced through variation of the volumetric airflow through the first compartment of the cartridge relative to the volumetric airflow through the second compartment of the cartridge. The ratio of the volumetric airflow through the first compartment relative to the volumetric airflow through the second compartment may be controlled through variation of one or more of the number, dimensions and location of the apertures forming the first air outlet of the first compartment of the cartridge relative to the number, dimensions and location of the apertures forming the second air outlet of the second compartment of the cartridge.

The flow area of the first air outlet of the first compartment may be the same as or different to the flow area of the second air outlet of the second compartment of the cartridge. The flow area of the second air outlet of the second compartment of the cartridge may be greater than flow area of the first air outlet of the first compartment of the cartridge.

Increasing the flow area of the second air outlet of the second compartment of the cartridge relative to the flow area of the first air outlet of the first compartment of the cartridge may advantageously increase the volumetric airflow through the second air outlet compared to the volumetric airflow through the first air outlet.

In embodiments in which the acid source comprises lactic acid, the ratio of the flow area of the first air outlet of the first compartment of the cartridge to the flow area of the second air outlet of the second compartment of the cartridge is preferably between about 3:4 and about 1:2. More preferably, the ratio of the flow area of the first air outlet of the first compartment of the cartridge to the flow area of the second air outlet of the second compartment of the cartridge is between about 2:3 and about 1:2.

In embodiments in which the flow area of the second air outlet of the second compartment of the cartridge is greater than flow area of the first air outlet of the first compartment of the cartridge, the flow area of the second air outlet of the second compartment of the cartridge may be increased relative to the flow area of the first air outlet of the first compartment of the cartridge by one or both of increasing the size of the one or more apertures forming the second air outlet relative to the size of the one or more apertures forming the first air outlet and increasing the number of apertures forming the second air outlet relative to the number of apertures forming the first air outlet.

Advantageously, the flow area of the second air outlet of the second compartment of the cartridge is increased relative to the flow area of the first air outlet of the first compartment of the cartridge by increasing the number of apertures forming the second air outlet relative to the number of apertures forming the first air outlet.

The first air inlet and the first air outlet of the first compartment of the cartridge may comprise the same or different numbers of apertures. Advantageously, the first air inlet and the first air outlet of the first compartment of the cartridge comprise the same numbers of apertures. Providing a first compartment having a first air inlet and a first air outlet comprising the same number of apertures may advantageously simplify manufacturing of the cartridge.

The second air inlet and the second air outlet of the second compartment of the cartridge may comprise the same or different numbers of apertures. Advantageously, the second air inlet and the second air outlet of the second compartment of the cartridge comprise the same numbers of apertures. Providing a second compartment having a second air inlet and a second air outlet comprising the same number of apertures may advantageously simplify manufacturing of the cartridge. Advantageously, the flow area of the first air outlet of the first compartment of the cartridge is between about 0.1 square millimetres and about 5 square millimetres.

In embodiments in which the first air outlet of the first compartment of the cartridge comprises a plurality of apertures, the apertures may have different flow areas so that the flow area of the first air outlet of the first compartment of the cartridge is divided unequally between the apertures forming the first air outlet.

In embodiments in which the first air outlet of the first compartment of the cartridge comprises a plurality of apertures, each of the apertures may have the same flow area so that the flow area of the first air outlet of the first compartment of the cartridge is divided equally between the apertures forming the first air outlet. Providing a first compartment having a first air outlet comprising a plurality of apertures having substantially the same flow area may advantageously simplify manufacturing of the cartridge.

The first air outlet of the first compartment of the cartridge may comprise one or more apertures having any suitable cross-sectional shape. For example, the cross-sectional shape of each aperture may be circular, elliptical, square or rectangular. In embodiments in which the first air outlet of the first compartment of the cartridge comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the first air inlet of the first compartment of the cartridge may be the same as or different to the dimensions of the one or more apertures forming the first air outlet of the first compartment of the cartridge.

Advantageously, the dimensions of the one or more apertures forming the first air inlet of the first compartment of the cartridge may be substantially the same as the dimensions of the one or more apertures forming the first air outlet of the first compartment of the cartridge. Providing a first compartment having a first air inlet and a first air outlet comprising one or more apertures of substantially the same dimensions may advantageously simplify manufacturing of the cartridge. Advantageously, the dimensions of the one or more apertures forming the first air outlet of the first compartment of the cartridge may be greater than the dimensions of the one or more apertures forming the first air inlet of the first compartment of the cartridge. Increasing the dimensions of the apertures forming the first air outlet of the first compartment of the cartridge relative to the dimensions of the apertures forming the first air inlet of the first compartment of the cartridge may advantageously reduce the risk of the first air outlet of the first compartment of the cartridge becoming obstructed by, for example, dust.

Advantageously, the flow area of the second air outlet of the second compartment of the cartridge is between about 0.1 square millimetres and about 5 square millimetres.

In embodiments in which the second air outlet of the second compartment of the cartridge comprises a plurality of apertures, the apertures may have different flow areas so that the total flow area of the second air outlet of the second compartment of the cartridge is divided unequally between the apertures forming the second air outlet.

In embodiments in which the second air outlet of the second compartment of the cartridge comprises a plurality of apertures, each of the apertures may have the same flow area so that the total flow area of the second air outlet of the second compartment of the cartridge is divided equally between the apertures forming the second air outlet. Providing a second compartment having a second air outlet comprising a plurality of apertures having substantially the same flow area may advantageously simplify manufacturing of the cartridge.

The second air outlet of the second compartment of the cartridge may comprise one or more apertures having any suitable cross-sectional shape. For example, the cross-sectional shape of each aperture may be circular, elliptical, square or rectangular. In embodiments in which the second air outlet of the second compartment of the cartridge comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the second air inlet of the second compartment of the cartridge may be the same as or different to the dimensions of the one or more apertures forming the second air outlet of the second compartment of the cartridge.

Advantageously, the dimensions of the one or more apertures forming the second air inlet of the second compartment of the cartridge may be substantially the same as the dimensions of the one or more apertures forming the second air outlet of the second compartment of the cartridge. Providing a second compartment having a second air inlet and a second air outlet comprising one or more apertures of substantially the same dimensions may advantageously simplify manufacturing of the cartridge.

Advantageously, the dimensions of the one or more apertures forming the second air outlet of the second compartment of the cartridge may be greater than the dimensions of the one or more apertures forming the second air inlet of the second compartment of the cartridge. Increasing the dimensions of the apertures forming the second air outlet of the second compartment of the cartridge relative to the dimensions of the apertures forming the second air inlet of the second compartment of the cartridge may advantageously reduce the risk of the second air outlet of the second compartment of the cartridge becoming obstructed by, for example, dust.

Advantageously, the first compartment has a longitudinal first air outlet and the second compartment has a longitudinal second air outlet.

As used herein with reference to the invention, the term "longitudinal air outlet" is used to describe one or more apertures through which air may be drawn in a longitudinal direction out of a component or portion of a component of the cartridge.

Advantageously, prior to first use of the cartridge, one or both of the first air outlet of the first compartment and the second air outlet of the second compartment may be sealed by one or more removable or frangible barriers. For example, one or both of the first air outlet of the first compartment and the second air outlet of the second compartment may be sealed by one or more peel-off or pierceable seals.

The one or more removable or frangible barriers may be formed from any suitable material. For example, the one or more removable or frangible barriers may be formed from a metal foil or film.

Advantageously, prior to first use of the cartridge, the first air inlet and the first air outlet of the first compartment of the cartridge and the second air inlet and the second air outlet of the second compartment of the cartridge are sealed by one or more removable or frangible barriers.

The cartridge may further comprise a third compartment downstream of the first compartment and the second compartment and in fluid communication with the first air outlet of the first compartment and the second air outlet of the second compartment. The nicotine vapour in the first air stream may react with the acid vapour in the second air stream in the third compartment to form an aerosol of nicotine salt particles.

In embodiments in which the cartridge further comprises a third compartment, the third compartment may comprise one or more aerosol-modifying agents. For example, the third compartment may comprise one or more sorbents, one or more flavourants, one or more chemesthetic agents or a combination thereof.

The first compartment and the second compartment may be arranged symmetrically with respect to each other within the cartridge.

Advantageously, the cartridge is an elongate cartridge. In embodiments in which the cartridge is an elongate cartridge and the substrate compartment comprises first and second compartments, the first compartment and the second compartment of the cartridge may be arranged symmetrically about the longitudinal axis of the cartridge.

The cartridge may have any suitable shape. For example, the cartridge may be substantially cylindrical. The cartridge may have any suitable transverse cross-sectional shape. For example, the transverse cross-sectional shape of the cartridge may be circular, semi-circular, elliptical, triangular, square, rectangular or trapezoidal.

The cartridge may have any suitable size.

For example, the cartridge may have a length of between about 5 millimetres and about 50 millimetres. Advantageously, the cartridge may have a length between about 10 millimetres and about 20 millimetres.

For example, the cartridge may have a width of between about 4 millimetres and about 10 millimetres and a height of between about 4 millimetres and about 10 millimetres. Advantageously, the cartridge may have a width of between about 6 millimetres and about 8 millimetres and a height of between about 6 millimetres and about 8 millimetres.

Cartridges for use in aerosol-generating systems according to the present invention may be formed by any suitable method. Suitable methods include, but are not limited to, deep drawing, injection moulding, blistering, blow forming and extrusion.

In preferred embodiments the cartridge is substantially cylindrical and comprises a first compartment, a second compartment and, where present, a third compartment which extend longitudinally between the opposed substantially planar end faces of the cylindrical cartridge.

The cartridge may be designed to be disposed of once the nicotine in the first compartment and the acid in the second compartment are depleted. The cartridge may be designed to be refillable. In preferred embodiments, the cartridge is consumable and the aerosol-generating device is reusable.

Advantageously, the cartridge comprises a body portion and one or more end caps.

The cartridge may comprise a body portion and a distal end cap.

The cartridge may comprise a body portion and a proximal end cap.

The cartridge may comprise a body portion, a distal end cap and a proximal end cap.

In embodiments in which the cartridge comprises a distal end cap, one or more apertures forming a first air inlet of a first compartment of the cartridge and one or more apertures forming a second air inlet of a second compartment of the cartridge may be provided in the distal end cap. In embodiments in which the cartridge comprises a proximal end cap, one or more apertures forming a first air outlet of a first compartment of the cartridge and one or more apertures forming a second air outlet of a second compartment of the cartridge may be provided in the proximal end cap.

The cartridge may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

In embodiments in which the cartridge comprises a body portion and one or more end caps, the body portion and the one or more end caps may be formed from the same or different materials. The cartridge may be formed from one or more materials that are nicotine-resistant and acid-resistant.

Where the cartridge comprises two or more aerosol-forming substrates, such as a nicotine source and an acid source, stored in a first compartment and a second compartment, the first compartment of the cartridge may be coated with one or more nicotine-resistant materials and the second compartment of the cartridge may be coated with one or more acid-resistant materials.

Examples of suitable nicotine-resistant materials and acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins and combinations thereof.

Use of one or more nicotine-resistant materials to one or both of form the cartridge and coat the interior of a first compartment of the cartridge may advantageously enhance the shelf life of the cartridge. Use of one or more acid-resistant materials to one or both of form the cartridge and coat the interior of a second compartment of the cartridge may advantageously enhance the shelf life of the cartridge.

The cartridge may be formed from one or more thermally conductive materials.

Where the cartridge comprises one or more aerosol-forming substrates, such as a nicotine source and an acid source, stored in a first compartment and a second compartment, the first compartment of the cartridge and the second compartment of the cartridge may be coated with one or more thermally conductive materials. Use of one or more thermally conductive materials to one or both of form the cartridge and coat the interior of a first compartment and a second compartment of the cartridge may advantageously increase heat transfer from the electric heater to the nicotine source and the acid source.

Suitable thermally conductive materials include, but are not limited to, metals such as, for example, aluminium, chromium, copper, gold, iron, nickel and silver, alloys, such as brass and steel and combinations thereof.

One or both ends of the cartridge may be sealed by one or more frangible barriers.

Where the cartridge comprises one or more aerosol-forming substrates, such as a nicotine source and an acid source, stored in a first compartment and a second compartment, the first compartment comprising the nicotine source and the second compartment comprising the lactic acid source may be sealed by one or more frangible barriers.

The one or more frangible barriers may be formed from any suitable material. For example, the one or more frangible barriers may be formed from a metal foil or film. In such embodiments the aerosol-generating device preferably further comprises a piercing member configured to rupture the one or more frangible barriers.

Alternatively or in addition, one or both ends of the cartridge may be sealed by one or more removable barriers, such as one or more peel-off seals. Where the cartridge comprises one or more aerosol-forming substrates, such as a nicotine source and an acid source, stored in a first compartment and a second compartment, one or both of the first compartment comprising the nicotine source and the second compartment comprising the lactic acid source may be sealed by one or more removable barriers. For example, one or both of the first compartment comprising the nicotine source and the second compartment comprising the lactic acid source may be sealed by one or more peel-off seals.

The one or more removable barriers may be formed from any suitable material. For example, the one or more removable barriers may be formed from a metal foil or film.

In preferred embodiments in which the cartridge is substantially cylindrical, one or both of the opposed substantially planar end faces of the cartridge may be sealed by one or more frangible barriers.

The aerosol-generating system may further comprise a mouthpiece. The mouthpiece may form an aerosol-forming chamber. Where the cartridge comprises one or more aerosol-forming substrates, such as a nicotine source and an acid source, stored in a first compartment and a second compartment, nicotine vapour released from the nicotine source in the first compartment of the cartridge and acid vapour released from the acid source in the second compartment of the cartridge may react with one another in the gas phase in the mouthpiece to form an aerosol of nicotine salt particles.

The mouthpiece may be configured for engagement with the cartridge.

In embodiments in which the mouthpiece is configured for engagement with the cartridge, the combination of the cartridge and the mouthpiece may simulate the shape and dimensions of a combustible smoking article, such as a cigarette, a cigar, or a cigarillo. Advantageously, in such embodiments the combination of the cartridge and the mouthpiece may simulate the shape and dimensions of a cigarette.

The mouthpiece may be configured for engagement with the housing of the aerosol-generating device. The mouthpiece may be designed to be disposed of once the aerosol-forming substrate in the substrate compartment is depleted.

The mouthpiece may be designed to be reusable. In embodiments in which the mouthpiece is designed to be reusable, the mouthpiece may advantageously be configured to be removably attached to the cartridge or the housing of the aerosol-generating device.

The mouthpiece may comprise a filter. The filter may have a low particulate filtration efficiency or very low particulate filtration efficiency. Alternatively, the mouthpiece may comprise a hollow tube.

As used herein with reference to the invention, the terms "proximal", "distal", "upstream" and "downstream" are used to describe the relative positions of components, or portions of components, of the cartridge, the aerosol-generating device, and aerosol-generating system.

The aerosol-generating system according to the invention comprises a proximal end through which, in use, an aerosol of nicotine salt particles exits the aerosol-generating system for delivery to a user. The proximal end may also be referred to as the mouth end. In use, a user draws on the proximal end of the aerosol-generating system in order to inhale an aerosol generated by the aerosol-generating system. The aerosol-generating system comprises a distal end opposed to the proximal end.

When a user draws on the proximal end of the aerosol-generating system, air is drawn into the aerosol-generating system, passes through the cartridge and exits the aerosol-generating system at the proximal end thereof. Components, or portions of components, of the aerosol-generating system may be described as being upstream or downstream of one another based on their relative positions between the proximal end and the distal end of the aerosol-generating system.

As used herein with reference to the invention, the term "longitudinal" is used to describe the direction between the proximal end and the opposed distal end of the aerosol-generating system, the cartridge or the aerosol-generating device and the term "transverse" is used to describe the direction perpendicular to the longitudinal direction.

As used herein with reference to the present invention, by "length" is meant the maximum longitudinal dimension between the distal end and the proximal end of components, or portions of components, of the aerosol-generating system.

As used herein with reference to the invention, the terms "height" and "width" are used to describe the maximum transverse dimensions of components, or portions of components, of the cartridge or aerosol-generating system perpendicular to the longitudinal axis of the cartridge or aerosol-generating system. Where the height and width of components, or portions of components, of the cartridge or aerosol-generating system are not the same, the term "width" is used to refer to the larger of the two transverse dimensions perpendicular to the longitudinal axis of the cartridge or aerosol-generating system.

As used herein with reference to the invention, the term "elongate" is used to describe a component or portion of a component of the cartridge having a length greater than the width and height thereof.

According to a second aspect of the present invention, there is provided an aerosol-generating device for use with a cartridge comprising a cartridge body defining a substrate compartment and a heater cavity; and an aerosol-forming substrate positioned within the substrate compartment, the device comprising a housing defining a device cavity for receiving at least a portion of the cartridge body; an elongate electric heater located in the device cavity; and a thermally conductive sheath secured over the elongate electric heater such that the electric heater is substantially enclosed within the thermally conductive sheath along at least part of its length. The thermally conductive sheath and the electric heater are configured to extend into the heater cavity of the cartridge when the cartridge is received in the device cavity such that, in use, the substrate compartment of the cartridge is heated by the electric heater via the thermally conductive sheath.

According to a further aspect of the present invention, there is provided a thermally conductive sheath for use in an aerosol-generating system according to the first aspect or an aerosol-generating device according to the second aspect.

According to a third aspect of the present invention, there is provided a kit for an aerosol-generating system, the kit comprising one or more cartridges for an aerosol-generating system and one or more thermally conductive sheaths, wherein each cartridge comprises a cartridge body defining a substrate compartment and a heater cavity, and wherein each thermally conductive sheath is configured to extend into the heater cavity of one or more of the cartridges and, in use, to be secured over an elongate electric heater of an aerosol-generating such that the electric heater is substantially enclosed within the thermally conductive sheath along at least part of its length and the substrate compartment of the cartridge is heated by the electric heater via the thermally conductive sheath.

According to a fourth aspect of the present invention, there is provided a method of adapting an aerosol-generating device for use with a cartridge, comprising the steps of: providing a cartridge comprising a cartridge body defining a substrate compartment and a heater cavity, and an aerosol-forming substrate positioned within the substrate compartment; providing an aerosol-generating device comprising a housing defining a device cavity for receiving at least a portion of the cartridge body; an elongate electric heater located in the device cavity; selecting a thermally conductive sheath based on the dimensions of the heater cavity and the dimensions of the electric heater; securing the thermally conductive sheath over the electric heater such that the electric heater is substantially enclosed within the thermally conductive sheath along at least part of its length; and inserting the cartridge into the device cavity such that the thermally conductive sheath and the electric heater extend into the heater cavity of the cartridge and such that the thermally conductive sheath is in contact with both an outer surface of the electric heater and an inside surface of the heater cavity.

It should be clear that features described in relation to one aspect of the invention may be applicable to another aspect of the invention. In particular, it should be clear that features described in relation to the system of the first aspect may equally be applied to the device of the second aspect, the kit of the third aspect, or the method of the fourth aspect, and vice versa.

Embodiments of the invention will now be described, by way of example only, with reference to the accompanying drawings, in which.

Figure 1:
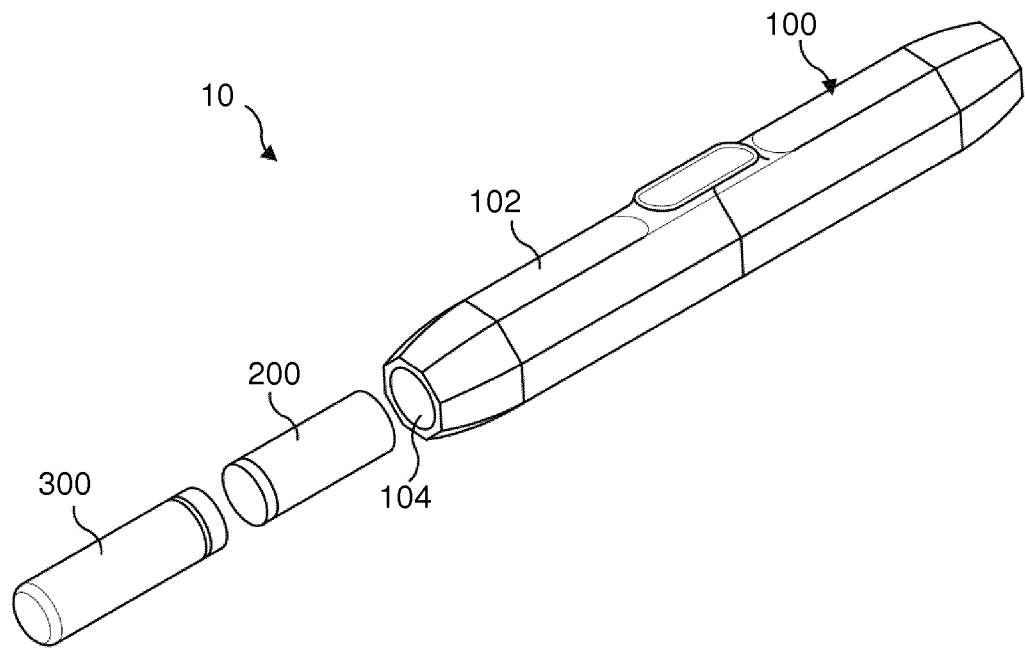
FIG. 1 shows an aerosol-generating system according to the invention.
Figure 3:
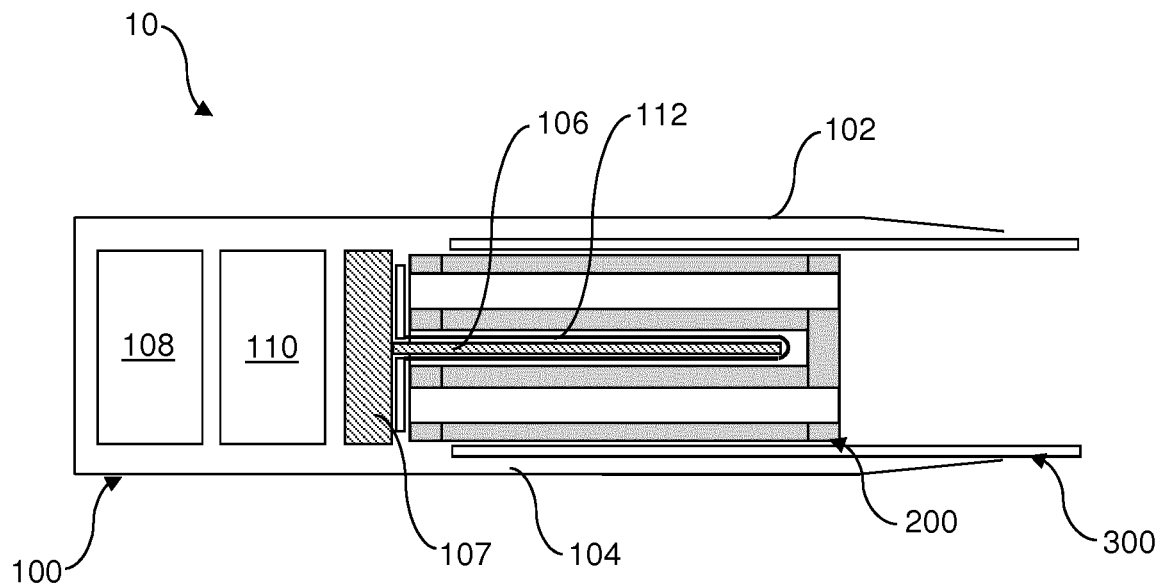
Figure 4:
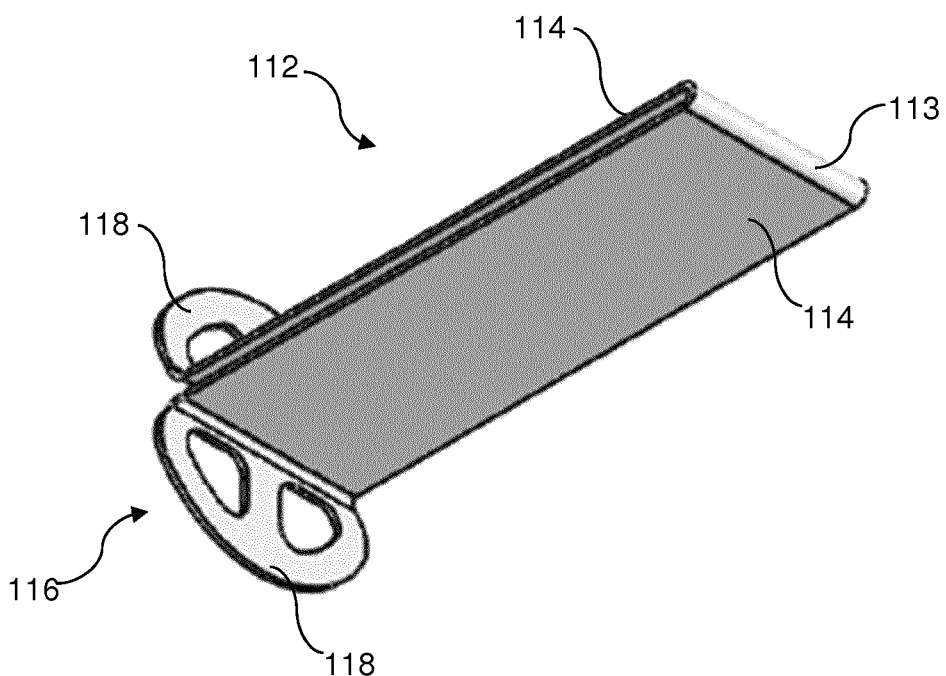
Figure 5:
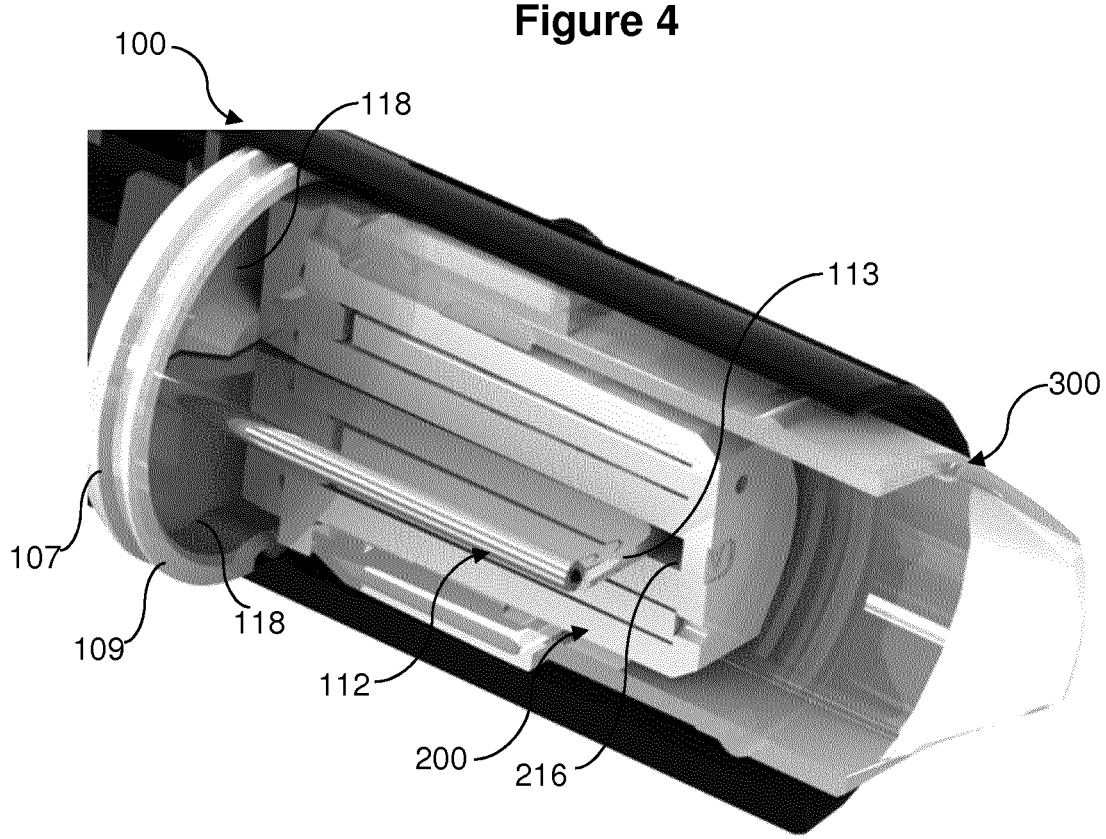
Figure 6:
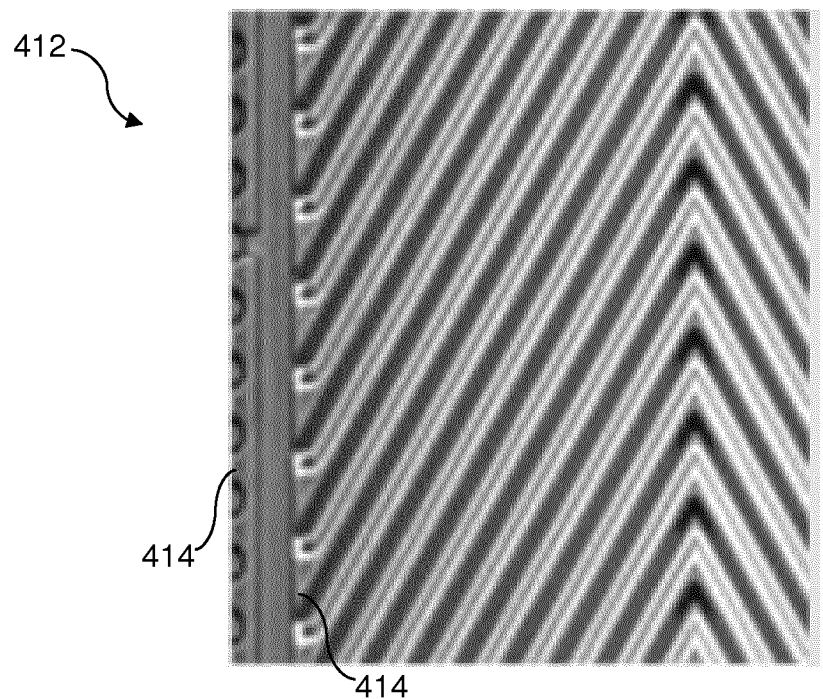
Figure 7:
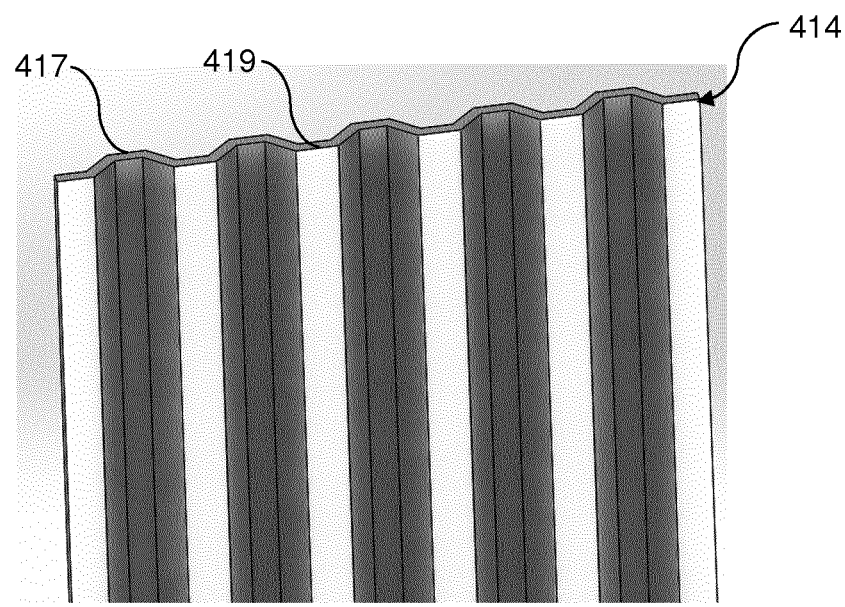

FIG. 3 schematically illustrates a longitudinal cross-section of the aerosol-generating system of FIG. 1 with the cartridge received in the aerosol-generating device;

FIG. 4 shows an enlarged view of a first embodiment of sheath;

FIG. 5 shows a partial cut-away view of the aerosol-generating system of FIG. 1 with the first embodiment of sheath positioned within the cartridge;

FIG. 6 shows an enlarged view of a portion of a second embodiment of sheath; and FIG. 7 illustrates a partial profile of the sheath of FIG. 6.

FIG. 1 shows a schematic illustration of an aerosol-generating system 10 according to the invention for generating an aerosol comprising nicotine lactate salt particles. The aerosol-generating system 10 comprises an aerosol-generating device 100, a cartridge assembly 200, and a mouthpiece 300.

Figure 2:
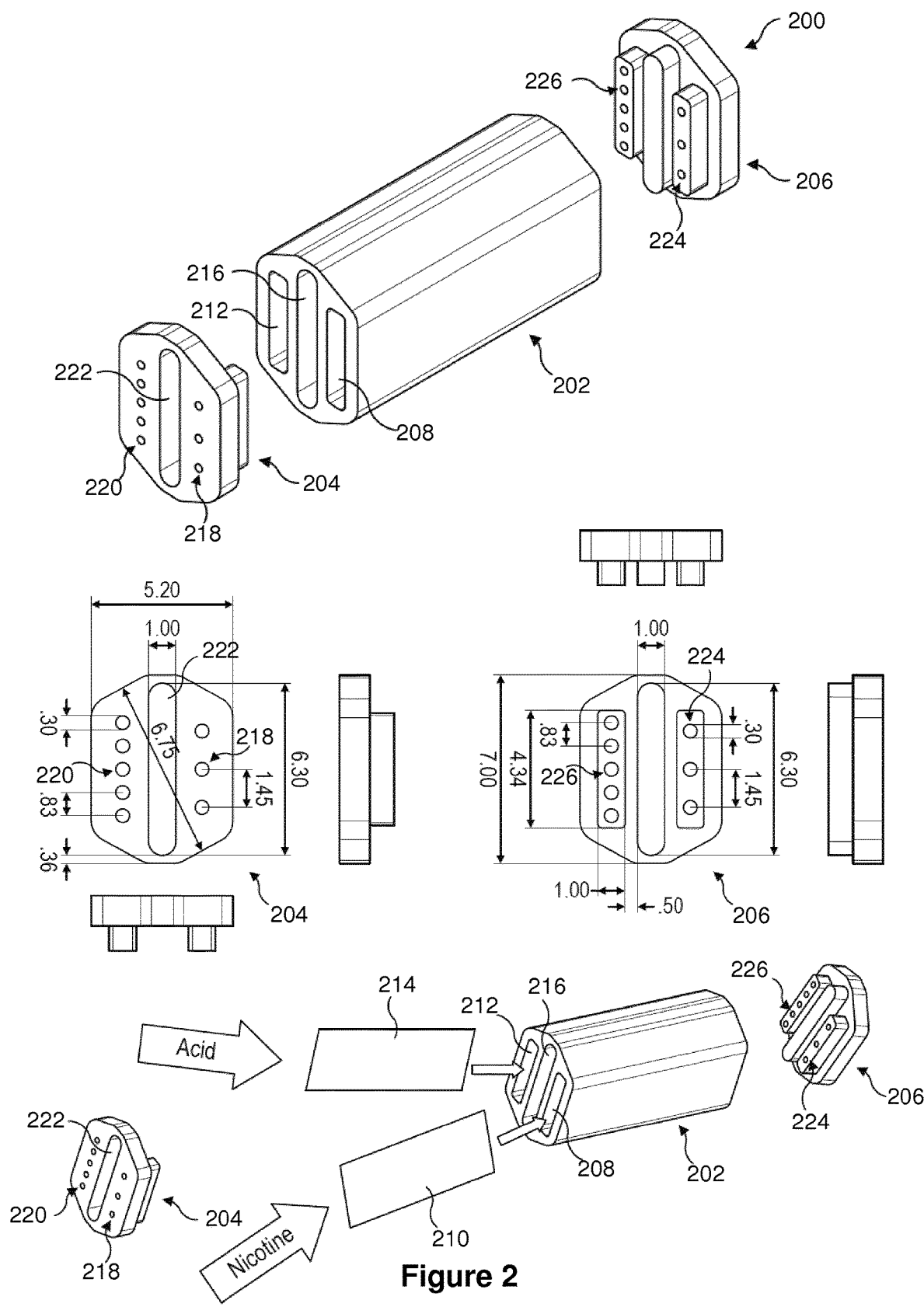
FIG. 2 shows a cartridge for use in the aerosol-generating system of FIG. 1.

FIG. 2 shows schematic illustrations of a cartridge assembly 200 for use in the aerosol-generating system of FIG. 1. The cartridge 200 comprises an elongate body 202, a distal end cap 204 and a proximal end cap 206 and has a length of about 15 millimetres, a width of about 7 millimetres and a height of about 5.2 millimetres. The body 202 has a length of about 13 millimetres, a width of about 7 millimetres and a height of about 5.2 millimetres. The distal end cap 204 and the proximal end cap 206 each have a length of about 2 millimetres, a width of about 7 millimetres and a height of about 5.2 millimetres.

The cartridge 200 comprises an elongate first compartment 208 that extends from the proximal end of the body 202 to the distal end of the body 202. The first compartment 208 contains a nicotine source comprising a first carrier material 210 impregnated with about 10 milligrams of nicotine and about 4 milligrams of menthol.

The cartridge 200 also comprises an elongate second compartment 212 that extends from the proximal end of the body 202 to the distal end of the body 202. The second compartment 212 contains a lactic acid source comprising a second carrier material 214 impregnated with about 20 milligrams of lactic acid.

The first compartment 208 and the second compartment 212 are arranged in parallel.

The cartridge 200 further comprises a heater cavity 216 for receiving an electric heater of the aerosol-generating device, which is configured to heat the first compartment 208 and the second compartment 212. The cavity 216 is located between the first compartment 208 and the second compartment 212 and extends from the proximal end of the body 202 to the distal end of the body 202. The cavity 216 is of substantially stadium shaped transverse cross-section and has a width of about 6.3 millimetres and a height of about 1 millimetre.

The distal end cap 204 comprises a first air inlet 218 comprising a row of three spaced apart apertures and a second air inlet 220 comprising a row of five spaced apart apertures. Each of the apertures forming the first air inlet 218 and the second air inlet 220 is of substantially circular transverse cross-section and has a diameter of about 0.3 millimetres. The flow area of the first air inlet 218 is about 0.21 square millimetres and the flow area of the second air inlet 220 is about 0.35 square millimetres. The ratio of the flow area of the first air inlet 218 to the flow area of the second air inlet 220 is about 3:5. The distal end cap 204 further comprises a third inlet 222 located between the first air inlet 218 and the second air inlet 220. The third inlet 222 is of substantially stadium shaped transverse cross-section and has a width of about 6.3 millimetres and a height of about 1 millimetre.

The proximal end cap 206 comprises a first air outlet 224 comprising a row of three spaced apart apertures and a second air outlet 226 comprising a row of five spaced apart apertures. Each of the apertures forming the first air outlet 224 and the second air outlet 226 is of substantially circular transverse cross-section and has a diameter of about 0.3 millimetres. The flow area of the first air outlet 224 is about 0.21 square millimetres and the flow area of the second air outlet 226 is about 0.35 square millimetres. The ratio of the flow area of the first air outlet 224 to the flow area of the second air outlet 226 is about 3:5.

To form the cartridge 200, the proximal end cap 206 is inserted into the proximal end of the body 202 such that the first air outlet 224 is aligned with the first compartment 208 and the second air outlet 226 is aligned with the second compartment 212. The first carrier material 210 impregnated with nicotine and menthol is inserted into the first compartment 208 and the second carrier material 214 impregnated with lactic acid is inserted into the second compartment 212. The distal end cap 204 is then inserted into the distal end of the body 202 such that the first air inlet 218 is aligned with the first compartment 208, the second air inlet 220 is aligned with the second compartment 212 and the third inlet 222 is aligned with the heater cavity 216.

The first compartment 208 and the second compartment 212 are substantially the same shape and size. The first compartment 208 and the second compartment 212 are of substantially rectangular transverse cross-section and have a length of about 11 millimetres, a width of about 4.3 millimetres and a height of about 1 millimetres. The first carrier material 210 and the second carrier material 214 comprise a non-woven sheet of PET/PBT and are substantially the same shape and size. The shape and size of the first carrier material 210 and the second carrier material 214 is similar to the shape and size of the first compartment 208 and the second compartment 212 of the cartridge 2, respectively.

The first air inlet 218 is in fluid communication with the first air outlet 224 so that a first air stream may pass into the cartridge 200 through the first air inlet 218, through the first compartment 208 and out of the cartridge 200 though the first air outlet 224. The second air inlet 220 is in fluid communication with the second air outlet 226 so that a second air stream may pass into the cartridge 200 through the second air inlet 220, through the second compartment 212 and out of the cartridge 2 though the second air outlet 226.

Prior to first use of the cartridge 200, the first air inlet 218 and the second air inlet 220 may be sealed by a removable peel-off foil seal or a pierceable foil seal (not shown) applied to the external face of the distal end cap 204. Similarly, prior to first use of the cartridge 200, the first air outlet 224 and the second air outlet 226 may be sealed by a removable peel-off foil seal or a pierceable foil seal (not shown) applied to the external face of the proximal end cap 206.

FIG. 3 schematically illustrates a longitudinal cross-section of the aerosol-generating system 10 of FIG. 1 with the cartridge 200 received in the aerosol-generating device 100. As shown in FIG. 3, the aerosol-generating device 100 comprises a device housing 102 defining a device cavity 104 for receiving the cartridge 200 and an upstream portion of the mouthpiece 300 which is engaged with the cartridge 200. The aerosol-generating device 100 further comprises an elongate electric heater 106 extending from a base portion 107, an electrical power supply 108, and a controller 110 for controlling a supply of electrical power from the electrical power supply 108 to the electric heater 106 via electrical contacts (not shown) on the base portion 107. The electric heater 106 is positioned centrally in the device cavity 104 and extends from the base portion 107 along the major axis of the device cavity 104. The electric heater 106 comprises an electrically insulating substrate and a resistive heating element positioned on the electrically insulating substrate. Positioned over the electric heater 106 is thermally conductive sheath 112 which forms a protective cover for the electric heater 106 and acts as a thermal bridge between the electric heater 106 and the cartridge 200 during use. In an alternative embodiment (not shown), the distal end of the mouthpiece 300 may be configured for engagement with the proximal end of the housing 102 of the aerosol-generating device 100 rather than the cartridge 200.

In use, the controller 110 controls a supply of electrical power from the electrical power supply 108 to the electric heater 106 to generate heat in the heating element which is then transferred to the cartridge 200 via the sheath 112 to heat the first compartment 208 and the second compartment 212 to an operating temperature of around 120 degrees Celsius. The thermally conductive sheath spreads heat from the electric heater across its outer surface to ensure more homogenous heating of the cartridge relative to arrangements in which no sheath is present. To bring the cartridge up to the operating temperature as quickly as possible, a preheat profile is applied to heat the heating element to about 200 degrees Celsius for around 30 seconds. After preheating, the temperature of the heating element is reduced to a substantially constant temperature of around 140 degrees Celsius.

When a user draws on the proximal end of the mouthpiece 300, air is drawn through the aerosol-generating system 10 through system airflow inlets extending through the housing 102 of the aerosol-generating device 100. The air is directed to the upstream end of the device cavity 104 where a first air stream is drawn through the first compartment 208 of the cartridge 200 and a second air stream is drawn through the second compartment 212 of the cartridge 200. As the first air stream is drawn through the first compartment 208, nicotine vapour is released from the first carrier material 210 into the first air stream. As the second air stream is drawn through the second compartment 212, lactic acid vapour is released from the second carrier material 214 into the second air stream. The nicotine vapour in the first air stream and the lactic acid vapour in the second air stream react with one another in the gas phase in the mouthpiece 300 to form an aerosol of nicotine salt particles, which is delivered to the user through the proximal end of the mouthpiece 300.

FIG. 4 shows the sheath 112 of the aerosol-generating device 100 in more detail. The sheath 112 is formed from a flat metal sheet which is wider than the electric heater 106 and which has been bent into a U-shape along a bend line 113 such that the sheath 112 comprises two opposed sheath walls 114. The sheath 112 is provided with a sheath mount 116 at its distal end by which the sheath 112 may be held in position over the electric heater 106. In this example, the sheath mount 116 comprises two sheath mount portions 118, each provided at the distal end of one of the sheath walls 114 and configured such that the sheath mount 116 is generally disc-shaped when the sheath walls 114, and thus the sheath mount portions 118, are brought together. The sheath mount portions 118 are made of a material having a high temperature resistance and preferably having low thermal conductivity, such as PEEK. In this example, the metal sheet from which the sheath 112 is formed is bent along a bend line 113 which is transverse to the longitudinal axis of the sheath 112 and is located at the proximal end of the sheath 112. In other examples, the bend line may have a different position or orientation. For example the metal sheet may be bent along a bend line which is parallel to the longitudinal axis of the sheath and extends along a side edge of the sheath. The bend line 113 provides a spring force to bias the sheath walls 114 slightly apart at the distal end of the sheath 112. This may improve the ease with which the sheath 112 is positioned over the electric heater 106. The metal sheet from which the sheath 112 is made may have any suitable thickness. In this example, the metal sheet has a sheet thickness of 0.27 mm.

In other examples, the metal sheet may have a different thickness depending on the dimensions of the electric heater and the cavity in the cartridge, along with the acceptable level of insertion and removal force of the cartridge for a given configuration.

FIG. 5 shows a partial cut-away view of the aerosol-generating system 10 in which the sheath 112 is positioned over the electric heater and within the heater cavity 216 of the cartridge 200. To secure the sheath 112 within the device cavity 104, the sheath walls 114 are positioned on either side of the electric heater and pinched together against the spring force at the bend line 113 so that the electric heater is sandwiched between and covered by the sheath walls 114. The sheath 112 is then pushed towards the distal end of the device cavity 104 to press-fit the sheath mount portions 118 against the inner diameter of a raised lip 109 extending around the base portion 107. In this manner, the sheath mount portions 118 are retained securely in the base portion 107 and the electric heater is clamped between the sheath walls 114. The cartridge 200 is then inserted into the cavity 104 along with the mouthpiece 300 such that the electric heater 106 and the sheath 112 extend into the heater cavity 216 of the cartridge 200. The sheath 112 protects the electric heater during insertion of the cartridge and is dimensioned such that the sheath walls 114 are in direct contact with the inner surface of the heater cavity 216. Thus, the thermally conductive sheath 112 acts as a thermal bridge between the electric heater and the cartridge and adapts the shape of the electric heater to the heater cavity 216 of the cartridge 200.

FIG. 6 illustrates an enlarged view of a portion of an alternative embodiment of sheath 412. Unlike the smooth, flat profile of the sheath of the first embodiment, the sheath 412 is formed from a metal sheet having a corrugated profile. This can be seen more clearly in FIG. 7, which illustrates the profile of one of the sheath walls 414 of the sheath 412. As shown, the corrugations form a plurality of corrugation peaks 417 and troughs 419 on the outer surface of each of the walls 414 of the sheath 412. The corrugations allow the sheath walls 414 to flex to conform to the inner surface of the heater cavity of the cartridge. This may improve the consistency of thermal contact between the electric heater and the cartridge by compensating for the manufacturing tolerances of the electric heater, the sheath, and the cartridge. This may help to ensure more consistent performance between different cartridges or different devices. Depending on their orientation, the corrugations may also increase the moment of inertia of the sheath relative to a flat sheet having the same sheet thickness. This increases the stiffness of the sheath and may reduce the risk of bending of the electric heater and the sheath during insertion of the cartridge into the device cavity. It may also decrease the amount of material required to manufacture a sheath of a given stiffness or thickness. In the embodiment shown in FIG. 6, the corrugations are arranged in a chevron pattern so that each corrugation extends in two different directions. By arranging the corrugations such that they extend in at least two different directions, the stiffness of the sheath 412 may be maintained in all directions. This differs from an arrangement in which each corrugation extends in a single direction across the entire width or length of the sheath. In such arrangements, the sheath will be more susceptible to bending if a bending moment is applied around an axis which is parallel to the corrugation direction.

The specific embodiments and examples described above illustrate but do not limit the invention. It is to be understood that other embodiments of the invention may be made and the specific embodiments and examples described herein are not exhaustive.

The invention claimed is:

1. An aerosol-generating device for an aerosol-generating system, the aerosol-generating device comprising:
   a housing defining a device cavity configured to receive at least a portion of an aerosol-generating article;
   an elongate electric heater disposed in the device cavity; and
   a thermally conductive sheath secured over the elongate electric heater such that the elongate electric heater is substantially enclosed within the thermally conductive sheath along at least part of a length of the elongate electric heater, the thermally conductive sheath having a thermal conductivity of at least 40 W/m·K as measured in accordance with ASTM C1114-00,
   wherein the thermally conductive sheath and the elongate electric heater are configured to extend into the aerosol-generating article when the aerosol-generating article is received in the device cavity such that, in use, the aerosol-generating article is heated by the elongate electric heater via the thermally conductive sheath.

2. The aerosol-generating device according to claim 1, wherein the thermally conductive sheath is permanently secured over the elongate electric heater.

3. The aerosol-generating device according to claim 1, wherein the thermally conductive sheath is removably secured over the elongate electric heater.

4. The aerosol-generating device according to claim 1, wherein the elongate electric heater is substantially enclosed within the then ially conductive sheath along substantially an entire length of the elongate electric heater.

5. The aerosol-generating device according to claim 1, wherein the thermally conductive sheath is thermally coupled to the elongate electric heater via one or more intermediate components.

6. The aerosol-generating device according claim 1, wherein the thermally conductive sheath is formed from a metal or alloy.

7. The aerosol-generating device according to claim 1, wherein the thermally conductive sheath is provided with a sheath mount by which the thermally conductive sheath is secured over the elongate electric heater.

8. The aerosol-generating device according to claim 7, wherein the sheath mount is made from a high temperature resistant material having a low thermal conductivity.

9. The aerosol-generating device according to claim 1, wherein the thermally conductive sheath comprises a single sheet of thermally conductive material which has been bent or folded into shape.

10. The aerosol-generating device according to claim 9, wherein the thermally conductive sheath comprises a sheet of thermally conductive material, which has been bent or folded along a bend line such that the sheath comprises two opposed sheath walls, between which the elongate electric heater is substantially enclosed along at least part of its length, and an opening opposite the bend line.

11. The aerosol-generating device according to claim 10, wherein the sheet of thermally conductive material is elastic and has been bent or folded such that the bend line provides a spring force to bias the sheath walls apart at the opening.

12. The aerosol-generating device according to claim 10, wherein the bend line is parallel to a longitudinal axis of the thermally conductive sheath and extends along a side edge of the thermally conductive sheath.

13. The aerosol-generating device according to claim 1, wherein the thermally conductive sheath comprises a corrugated sheet of thermally conductive material.

14. The aerosol-generating device according to claim 13, wherein the corrugated sheet of thermally conductive material comprises a first set of corrugations extending along a first direction and a second set of corrugations extending along a second direction, which is at an angle to the first direction.

15. The aerosol-generating device according to claim 1, wherein the thermally conductive sheath has a thickness of from about 0.20 mm to about 0.35 mm.

16. The aerosol-generating device according to claim 1, wherein the thermally conductive sheath has a thickness of from about 0.22 mm to about 0.30 mm.

17. The aerosol-generating device according to claim 1, wherein the thermally conductive sheath has a thickness of from about 0.25 mm to about 0.29 mm.

18. The aerosol-generating device according to claim 1, wherein the thermally conductive sheath has a thickness of about 0.27 mm.

* * * * *